United States Patent [19]

Dillman

[11] 4,382,862
[45] May 10, 1983

[54] BACTERIA-REMOVING CARTRIDGE AND PREPARATORY PROCESS

[75] Inventor: Terry R. Dillman, Rockford, Ill.

[73] Assignee: Illinois Water Treatment Company, Rockford, Ill.

[21] Appl. No.: 261,837

[22] Filed: May 8, 1981

[51] Int. Cl.³ ............................................. B01D 15/04
[52] U.S. Cl. ..................... 210/668; 210/755; 210/282; 422/37; 436/125
[58] Field of Search ............... 210/668, 754, 755, 764, 210/266, 282, 283, 284, 287, 289, 501, 502; 422/3, 37, 70; 436/125

[56] References Cited

U.S. PATENT DOCUMENTS

| | | | |
|---|---|---|---|
| Re. 27,275 | 1/1972 | Dajani | 210/54 |
| Re. 29,241 | 5/1977 | Dajani | 210/54 |
| 1,713,251 | 5/1929 | Blumenberg, Jr. | 210/501 |
| 2,578,186 | 12/1951 | Ham | 260/3 |
| 2,792,942 | 5/1957 | Feuillet | 210/257 |
| 3,242,073 | 3/1966 | Guebert et al. | 210/64 |
| 3,244,710 | 4/1966 | Larsen | 260/248.5 |
| 3,312,588 | 4/1967 | Larsen | 167/33 |
| 3,316,173 | 4/1967 | Mills et al. | 210/754 |
| 3,327,859 | 6/1967 | Pall | 210/266 |
| 3,357,563 | 12/1967 | Sicard | 210/266 |
| 3,408,292 | 10/1968 | Dajani | 210/52 |
| 3,409,547 | 11/1968 | Dajani | 210/54 |
| 3,547,810 | 12/1970 | Cooper | 210/62 |
| 3,779,909 | 12/1973 | Wisfeld et al. | 210/29 |
| 3,817,860 | 6/1974 | Lambert et al. | 210/668 |
| 3,897,213 | 7/1975 | Stevens et al. | 210/284 |
| 3,923,665 | 12/1975 | Lambert et al. | 210/501 |
| 3,928,197 | 12/1975 | Horan, Jr. et al. | 210/62 |
| 3,948,858 | 4/1976 | Horning et al. | 260/67.6 R |
| 4,071,636 | 1/1978 | Nishino et al. | 427/2 |
| 4,076,622 | 2/1978 | Costin | 210/501 |
| 4,111,922 | 9/1978 | Beede et al. | 526/292 |
| 4,115,270 | 9/1978 | Phillips | 210/169 |
| 4,151,092 | 4/1979 | Grimm et al. | 210/256 |
| 4,152,262 | 5/1979 | Rose | 210/136 |
| 4,187,183 | 2/1980 | Hatch | 210/501 |
| 4,190,529 | 2/1980 | Hatch | 422/37 |
| 4,199,449 | 4/1980 | Slejko | 210/266 |
| 4,298,475 | 11/1981 | Gartner | 210/266 |

FOREIGN PATENT DOCUMENTS 1107768 3/1968 United Kingdom .

OTHER PUBLICATIONS

Bulletin DX-1079, of Illinois Water Treatment Company.
Bulletin IE-246, (Jun., 1978) of Rohm and Haas Company.
Slejko, et al., "Upgrading the Microbiological Quality of Process Deionized Water by Ion Exchange Filtration", Rohm and Haas Company.
Preconditioning Procedure for Ambergard ™ XE-352A Filter", Rohm and Haas Company.

*Primary Examiner*—Ivars C. Cintins
*Attorney, Agent, or Firm*—George R. Clark; Neil M. Rose; Robert J. Fox

[57] ABSTRACT

In a cartridge for removal of impurities from water, an elongated tube is charged, between water-permeable barriers, with ion exchange resin of a type capable of removal of bacteria from water. Outside one such barrier, an inlet cap is charged with water-soluble bactericide in a shelf-stable, water-activatable form. Preferably, the bactericide is sodium salt of dichloroisocyanuric acid, in granular form.

24 Claims, 3 Drawing Figures

BACTERIA-REMOVING CARTRIDGE AND PREPARATORY PROCESS

BACKGROUND OF THE INVENTION

This invention pertains to an improvement in a cartridge for removal of impurities from water. The improvement facilitates preparation of ion exchange resin, of a type capable of removal of bacteria from water, in a cartridge. This invention also pertains to a process for preparation of such a resin in a cartridge.

It is known for various adsorbing, absorbing, and filtering media including activated carbon and ion exchange resins of various types for removal of impurities from water to be packaged in disposable cartridges of a type comprising an elongated tube, water-permeable barriers disposed across each end of the elongated tube, a sealed cap having an inlet for water at one end of the elongated tube, and a sealed cap having an outlet for water at the other end. The inlet and the outlet are sealed, in shipment and storage, by removable seals. The elongated tube is charged between the respective barriers with a selected medium. Various cartridges, which are distinguished by their contents of various media, are available commercially from Illinois Water Treatment Company, Rockford, Ill. 61105, under its trademark IWT, and are described in Bulletin DX-1079 of Illinois Water Treatment Company.

As described in U.S. Pat. No. 4,199,449, it is known for large-pore macroreticular, Type 1, quaternary ammonium, anion exchange resins in various forms including chloride, sulfate, and hydroxide forms to be used to remove bacteria of various gram positive and gram negative types including *E. coli, S. faecalis,* and *Ps. aeruginosa* from water, which is to be used in manufacture of pharmaceuticals, in manufacture of cosmetics, and otherwise. Such resins are available commercially from Rohm and Haas Company, Philadelphia, Pa. 19105, under its trademark AMBERGARD, and are described in Bulletin 1E-246 (June, 1978) of Rohm and Haas Company, and in F. L. Slejko and C. R. Costin, "Upgrading the Microbiological Quality of Process Deionized Water by Ion Exchange Filtration", an undated paper (circa 1979) distributed by Rohm and Haas Company.

Before it is used, such a resin is pretreated with an aqueous solution of hydrochloric acid, which places the resin in proper ionic form, and which may sterilize the resin. However, the resin may become recontaminated with bacteria in storage, in handling of the resin, or otherwise.

A column of such a resin tends to become loaded with bacteria progressively from its inlet to its outlet. Bacteria loading a column of such a resin near its outlet tend to be washed out with water leaving the column. As bacteria from air-borne and other sources tend to be found throughout a column of such a resin unless aseptic conditions are maintained, it is known for a column of such a resin to be prepared by precolation of an aqueous solution of a suitable bactericide, as exemplified by sodium hypochlorite, through the column so as to kill bacteria found throughout the column, whereupon the aqueous solution must be rinsed from the column so as to eliminate residual contamination by the aqueous solution.

Additionally, it is known for large-pore macroreticular and other types of ion exchange resins to contain microbiocides, which may contain halogens, and which are bound either chemically or physically to the resins.

Pertinent references include U.S. Pat. No. 4,076,622, which deals with large-pore macroreticular ion exchange resins, and U.S. Pat. No. 4,190,529, U.S. Pat. No. 4,187,183, U.S. Pat. No. 3,187,860 and U.S. Pat. No. 3,316,173, which deal with various other ion exchange resins. As mentioned hereinbefore, U.S. Pat. No. 4,199,449 also is pertinent here.

Also, it is known for a soluble bactericide, which may contain chlorine, to be used in various apparatus for purification of water for drinking, swimming, etc. Typically, such apparatus yield water containing some dissolved bactericide. Exemplary references include U.S. Pat. No. 4,152,262, U.S. Pat. No. 4,151,092, U.S. Pat. No. 4,115,270, and U.S. Pat. No. 2,792,942.

SUMMARY OF THE INVENTION

This invention pertains to an improvement in a cartridge for removal of impurities from water, of a type comprising an elongated tube, a first barrier, which is permeable to water, and which is disposed across a first end of the elongated tube, a second barrier, which is permeable to water, and which is disposed across a second end of the elongated tube, a first cap, which has a cylindrical wall sealed to the elongated tube at its first end so as to enclose the first barrier, and which is closed except for an inlet for water, and a second cap, which has a cylindrical wall sealed to the elongated tube at its second end so as to enclose the second barrier, and which is closed except for an outlet for water.

The improvement contemplates that the elongated tube is charged, between the first barrier and the second barrier, with ion exchange resin of a type capable of removal of bacteria from water. The improvement also contemplates generally that one such cap is charged with water-soluble bactericide in a shelf-stable, water-activatable form, and particularly that the first cap is charged with such a bactericide, which is separated from the resin by the first barrier unless the bactericide permeates the first barrier in a solution.

This invention also pertains to a process for preparation of ion exchange resin of a type capable of removal of bacteria from water. The process comprises a step of providing a cartridge of the type admitting the improvement discussed hereinbefore, wherein the elongated tube is charged, between the first barrier and the second barrier, with the resin and wherein the first cap is charged with water-soluble bactericide in a shelf-stable, water-activatable form, which is separated from the resin by the first barrier unless the bactericide permeates the first barrier in a solution.

The process also comprises a step of connecting the inlet to a source of water, a step of dissolving the bactericide in water, which thus enters the cartridge from the source through the inlet, so as to enable the bactericide to permeate the first barrier, percolate through the resin, permeate the second barrier, and leave the cartridge through the outlet, in aqueous solution, a step of recovering water leaving the cartridge through the outlet, and a step of monitoring water being recovered, for positive indications of the bactericide in aqueous solution, until such indications cease to be found.

Once such indications cease to be found, until the cartridge becomes loaded with bacteria from the first barrier to the second barrier, bacteria tending to be washed out with water leaving the cartridge through the outlet tend to be few. Advantageously, the source may be a source of water from which bacteria are to be removed, as the bactericide in aqueous solution not only kills bacteria found in the resin but also kills bacteria carried in water from the source, so as to avoid any need for another source of water for the aqueous solution.

Common considerations apply to the improvement described hereinbefore and to the process described hereinbefore. The improvement enables the process to be practiced. The first cap of the cartridge may be charged with the bactericide in a granular form, which is preferred so as to facilitate dosage or in a caked form. Preferably, the bactericide contains chlorine, which in aqueous solution may be monitored easily by standard tests. Preferably, sodium salt of dichloroisocyanuric acid, $C_3N_3O_3Cl_2Na$, is used as the bactericide. As available in a technical grade, such salt is granular. The resin may be a large-pore macroreticular, Type 1, quaternary ammonium, anion exchange resin, whereupon the first cap may be charged with not less than approximately one gram of sodium salt of dichloroisocyanuric acid as the bactericide in a granular form, by dry weight, for each ten grams of the resin, by dry weight.

BRIEF DESCRIPTION OF THE DRAWINGS

FIG. 1 also shows fittings and conduits.

As shown in FIG. 2, an inlet of the cartridge and an outlet of the cartridge are sealed by removable seals, which are attached in shipment and storage, and which have been removed in FIG. 1.

DETAILED DESCRIPTION OF PREFERRED EMBODIMENT

Figure 1:
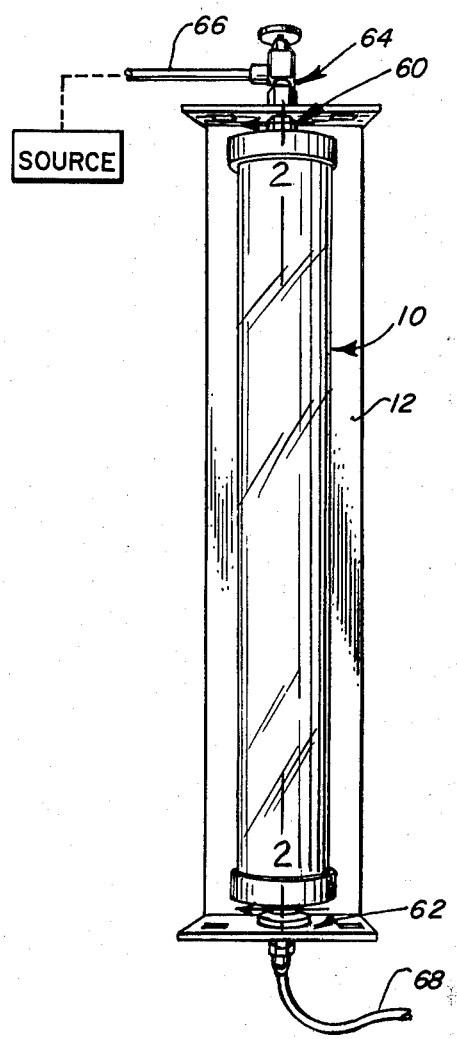
FIG. 1 is a front, perspective view of a cartridge embodying the improvement described hereinbefore, as mounted in a bracket, which may be mounted to a wall.

As shown in FIG. 1, a cartridge 10 for removal of bacteria from water is mounted in a bracket 12, which may be mounted to a wall. The cartridge 10 has a vertical orientation, which is conventional for prior cartridges for removal of impurities from water, but which is not essential.

Figure 2:
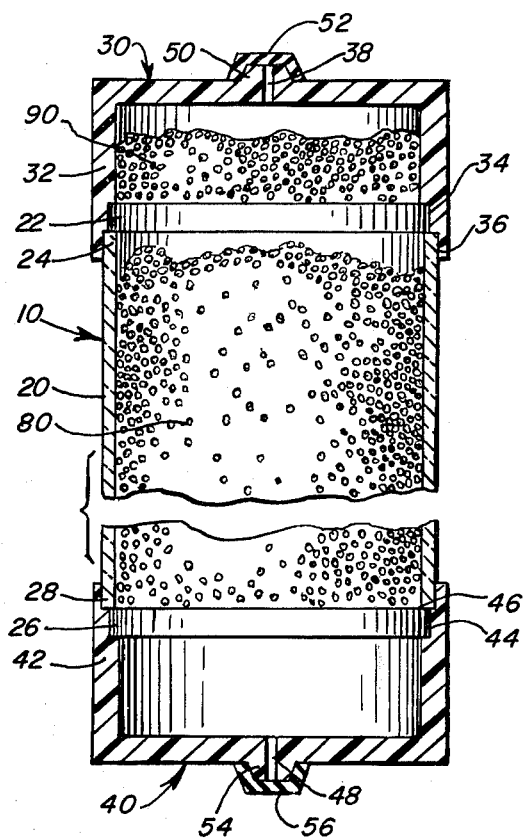
FIG. 2 is an axial, sectional view of the cartridge of FIG. 1, as taken along line 2—2 in a direction indicated by arrows, wherein the cartridge contains a bactericide in a granular form.

As shown in FIG. 2, the cartridge 10 comprises an elongated tube 20, which may be made of transparent, pressure-resistant, rigid polycarbonate, as available from General Electric Company, Bridgeport, Conn. 06602, under its trademark LEXAN, so as to allow visual inspection of its contents. Also, the cartridge 10 comprises a first barrier 22, which is permeable to water, which is disposed across a first end 24 of the elongated tube 20, and which may be a rigid disc of porous, high-density polyethylene, as available from Glasrock Plastics Group, Industrial Products Division, Fairburn, Ga. 30213.

Also, the cartridge 10 comprises a second barrier 26, which is permeable to water, which is disposed across a second end 28 of the elongated tube 20, and which may be a similar disc.

As shown in FIG. 2, the cartridge 10 comprises a first cap 30, which has a cylindrical wall 32. The cylindrical wall 32 has an inner step 34, which accommodates the first barrier 22, and an inner step 36, which accommodates the elongated tube 20 at its first end 24. After the cartridge 10 has been charged with resin and bactericide through the first end 24 of the elongated tube 20, the cylindrical wall 32 is welded ultrasonically to the elongated tube 20 so as to seal the first cap 30 to the elongated tube 20 at its first end 24. The first cap 30, which has an inlet 38 for water, encloses the first barrier 22 and closes the first end 24 of the elongated tube 20 except for the inlet 38. Also, the cartridge 10 comprises a second cap 40, which has a cylindrical wall 42. The cylindrical wall 42 has an inner step 44, which accommodates the second barrier 26, and an inner step 46, which accommodates the elongated tube 20 at its second end 28. Before the cartridge 10 is charged with resin and bactericide through the first end 24 of the elongated tube 20, the cylindrical wall 42 is welded ultrasonically to the elongated tube 20 so as to seal the second cap 40 to the elongated tube 20 at its second end 28. The second cap 40, which has an outlet 48 for water, encloses the second barrier 26 and closes the second end 28 of the elongated tube 20 except for the outlet 48.

As shown in FIG. 2, the first cap 30 has an external, conical boss 50, through which the inlet 38 extends, and a removable seal 52 is fitted onto the boss 50 so as to seal the inlet 38. Also, the second cap 40 has an external, conical boss 54 through which the outlet 48 extends, and a removable seal 56 is fitted onto the boss 54 so as to seal the outlet 48. The removable seal 52 and the removable seal 56 may be made of any suitable, elastomeric material, as exemplified by neoprene. The removable seal 52 and the removable seal 56 protect contents of the cartridge 10 against dehydration and contamination, in shipment and storage, and are removed before the cartridge 10 is mounted in the bracket 12.

As shown in FIG. 1, the boss 50 on the first cap 30 fits into upper fittings 60 on the bracket 12, and the boss 54 fits into lower fittings 62 on the bracket 12. The fittings 60 are connected, via a manual valve 64, to a conduit 66, which is adapted to be connected to a source (which is indicated diagrammatically in FIG. 1) of water from which bacteria are to be removed, under pressure not to exceed approximately 100 psig. The fittings 62 are connected to a conduit 68, which is adapted to be connected to a receiver (not shown) for water.

Precise details of the bracket 12, the fittings 60, the fittings 62, the valve 64, the conduit 66, and the conduit 68 are inessential to comprehension of this invention. As described so far, the cartridge 10, the bracket 12, the fittings 60, the fittings 62, the valve 64, the conduit 66, and the conduit 68 are similar to prior products sold by Illinois Water Treatment Company for removal of impurities other than bacteria from water.

Pursuant to this invention, the elongated tube 20 is charged, between the first barrier 22 and the second barrier 26, with ion exchange resin 80 of a type capable of removal of bacteria from water. As shown in FIG. 2, a bead form of the resin 80 is used. Preferably, the resin 80 is a large-pore macroreticular, Type 1, quaternary ammonium, anion exchange resin in chloride, sulfate, or hydroxide form, as discussed hereinbefore.

Pursuant to the invention, the first cap 30 is charged with water-soluble bactericide 90 in a shelf-stable, water-activatable form, which is separated from the resin 80 by the first barrier 22 unless the bactericide 90 permeates the first barrier 22 in a solution. Preferably, the bactericide 90 is sodium salt of dichloroisocyanuric acid, $C_3N_3O_3Cl_2Na$, which contains chlorine, as chlorine in aqueous solution may be monitored easily by standard tests. As available in a technical grade, such salt is granular.

If the resin 80 is a large-pore macroreticular, Type 1, quaternary ammonium, anion exchange resin, the first cap 30 may be charged with approximately one gram of sodium salt of dichloroisocyanuric acid, $C_3N_3O_3Cl_2Na$, as the bactericide 90 in a granular form, by dry weight, for each ten grams of the resin 80, by dry weight. The cartridge 10 may be charged with 300 grams of the resin 80, by dry weight, and with 30 grams of said salt, by dry weight, as the bactericide 90.

After the valve 64 has been opened so as to admit water from the source into the cartridge 10 through the conduit 66, through the fittings 60, and through the inlet 38, the bactericide 90 is dissolved so as to permeate the first barrier 22, percolate through the resin 80, permeate the second barrier 26, and leave the cartridge 10 through the outlet 48, in aqueous solution.

Water recovered from the outlet 48 is monitored, either continuously or intermittently, for positive indications of the bactericide in aqueous solution until such indications cease to be found. Once such indications cease to be found, until the cartridge 10 becomes loaded with bacteria from the first barrier 22 to the second barrier 26, bacteria tending to be washed out with water leaving the cartridge 10 through the outlet 48 tend to be few. Advantageously, the bactericide in aqueous solution not only kills bacteria found in the resin 80 but also kills bacteria carried in water from the source, so as to avoid any need for another source of water for the aqueous solution. Also, the bactericide in aqueous solution kills bacteria found in the cartridge 10, the second cap 40, which includes the outlet 48, the fittings 62, and the conduit 68.

Figure 3:
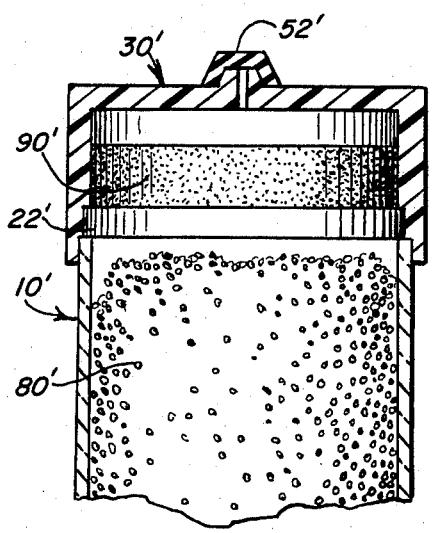
FIG. 3 is a similar, fragmentary view of one end of a cartridge of similar construction containing a bactericide in a caked form.

As shown in FIG. 2, the first cap 30 of the cartridge 10 is charged with the bactericide 90 in a granular form, which is preferred for ease of dosage. As shown in FIG. 3, a similar cap 30', which is associated with a similar barrier 22' and with a similar seal 52' at the inlet end of a cartridge 10' of similar construction, is charged with a bactericide 90' in a caked form.

Preferably, as discussed hereinabove, the bactericide is sodium salt of dichloroisocyanuric acid, $C_3N_3O_3Cl_2Na$. Alternatively, the bactericide may be calcium hypochlorite, $Ca(OCl)_2$. Other bactericides are suitable alternatives.

A standard method to detect free chlorine in water is the "DPD Colorimetric Method", Method 409F, as found in *Standard Methods for the Examination of Water and Wastewater,* 14th edition, American Public Health Association, 1976, and as available in kit form from Hach Chemical Company, P.O. Box 389, Loveland, Colo. 80537, as Kit Model CN-70 and Kit Model CN-66. Water recovered from the outlet 48 may be monitored, intermittently by such a method, for positive indications of free chlorine from sodium salt of dichloroisocyanuric acid, $C_3N_3O_3Cl_2Na$, in aqueous solution until such indications cease to be found.

A quantity of AMBERGARD XE 352A resin as received from Rohm and Haas Company, was charged into a column. Three bed volumes of a 10% aqueous solution of hydrochloric acid were passed through the resins. The resin then was rinsed with deionized water, which had been filtered through a 0.2 micron filter, until the resin was free of hydrochloric acid. The resin was then removed from the column. Excess water then was removed from the resin by suction filtration in a large Buchner funnel.

In a cartridge like the cartridge 10, the second barrier and the second (outlet) cap were sealed to the elongated tube of the cartridge. The cartridge then was hand-picked with the resin, which had been pretreated as noted in the preceding paragraph, whereupon 30 grams of sodium salt of dichloroisocyanuric acid were sealed between the first barrier and the first (inlet) cap, which then was sealed onto the elongated tube of the cartridge.

The cartridge was installed in a bracket like the bracket 12, so as to associate the first (inlet) cap with upper fittings like the fittings 60, and so as to associate the second (outlet) cap with lower fittings like the fittings 62. The cartridge then was connected, at the inlet of the first (inlet) cap, to a source of deionized water, which had been filtered through a 2.0 micron filter, and which rinsed the cartridge until its effluent stream was found to be devoid of free chlorine. The effluent stream was monitored for free chlorine by the "DPD Colorimetric Method" noted hereinabove.

After the effluent stream was found to be devoid of free chlorine, a sample of the effluent stream was collected in a sterile container. The sample was tested for total bacterial count by the standard membrane filter technique. The filter was incubated for 24 hours on "Total Count Medium with T.T.C. Indicator", as obtained in ampule form from Millipore Corporation, Bedford, Mass. 01730, whereupon no bacterial colonies were found.

As disclosed in a co-pending United States patent application filed simultaneously herewith by David E. Moyer, assigned commonly herewith, and entitled BACTERIA-REMOVING CARTRIDGE AND PREPARATORY PROCESS, it has been found that, unless the resin has been exposed to high levels of bacterial contamination after the resin has been pretreated with an aqueous solution of hydrochloric acid, it ordinarily is not necessary for the resin to be treated again with a bactericide after the cartridge has been charged with the resin and before the cartridge is used, as such a resin does not tend to slough bacteria at low levels of bacterial contamination.

This invention addresses not only potential risks of bacterial contamination of the resin, at both high and low levels, but also potential risks of bacterial contamination of the outlet cap and the fittings connected to the outlet cap.

I claim:

1. A cartridge for removal of impurities from water comprising
   (a) an elongated tube having a first end and a second end,
   (b) a first barrier, which is permeable to water, and which is disposed across the first end of the elongated tube,
   (c) a second barrier, which is permeable to water, and which is disposed across the second end of the elongated tube,
   (d) a first cap which has a cylindrical wall sealed to the elongated tube at the first end of the elongated tube so as to enclose the first barrier, and which is closed except for an inlet for water,
   (e) a second cap, which has a cylindrical wall sealed to the elongated tube at the second end of the elongated tube so as to enclose the second barrier, and which is enclosed except for an outlet for water,
   (f) an ion exchange resin of a type capable of removing bacteria from water, said ion exchange resin being charged between said first barrier and said second barrier within said elongated tube, (g) a highly water-soluble bactericide in a shelf-stable, water-activatable form charged in one of said caps, said highly water-soluble bactericide flushing downstream through one of said caps and said outlet when water is first introduced into said cartridge to sterilize portions of said cartridge located downstream of said bactericide, said bactericide being rapidly and completely expended so that following sterilization normal use of said cartridge allows said ion exchange resin to remove bacteria from water while preventing adulteration of said water with said bactericide.

2. The improvement of claim 1 wherein the first cap is charged with the bactericide, which is separated from the resin by the first carrier unless the bactericide permeates the first barrier in a solution.

3. The improvement of claim 1 or 2 wherein the first cap is charged with the bactericide in a granular form.

4. The improvement of claim 1 or 2 wherein the first cap is charged with the bactericide in a caked form.

5. The improvement of claim 1 or 2 wherein the bactericide contains chlorine.

6. The improvement of claim 5 wherein the bactericide is sodium salt of dichloroisocyanuric acid.

7. The improvement of claim 1 or 2 wherein the resin is a large-pore macroreticular, Type 1, quaternary ammonium, anion exchange resin.

8. The improvement of claim 7 wherein the bactericide is sodium salt of dichloroisocyanuric acid.

9. The improvement of claim 8 wherein the first cap is charged with not less than approximately one gram of sodium salt of dichloroisocyanuric acid as the bactericide in a granular form, by dry weight, for each ten grams of the resin, by dry weight.

10. A method of preparing an ion exchange resin of a type capable of removal of bacteria from water comprising steps of (a) providing a cartridge of a type comprising
  (1) an elongated tube having a first and a second end,
  (2) a first barrier, which is permeable to water, and which is disposed across the first end of the elongated tube,
  (3) a second barrier, which is permeable to water, and which is disposed across the second end of the elongated tube,
  (4) a first cap, which has a cylindrical wall sealed to the elongated tube at the first end of the elongated tube so as to enclose the first barrier, and which is closed except for an inlet of water, and
  (5) a second cap, which has a cylindrical wall sealed to the elongated tube at the second end of the elongated tube so as to enclose the second barrier, and which is closed except for an outlet for water, wherein the elongated tube is charged, between the first barrier and the second barrier, with the resin and wherein the first cap is charged with a highly water-soluble bactericide in a shelf-stable, water-activatable form, which is separated from the resin by the first barrier unless the bactericide permeates the first barrier in a solution, (b) connecting the inlet to a source of water,
(c) rapidly and completely dissolving the highly water-soluble bactericide in water, which thus enters the cartridge from the source through the inlet, so as to enable the bactericide to permeate the first barrier, percolate through the resin, permeate the second barrier, and leave the cartridge through the outlet, in aqueous solution, to effect rapid sterilization of a portion of said cartridge,
(d) recovering water leaving the cartridge through the outlet, and
(e) monitoring water being recovered, for positive indications of the bactericide in aqueous solution, until such indications cease to be found in order to ensure that subsequent operation of said cartridge to remove bacteria from water does not result in contamination of said water with bactericide.

11. The improvement of claim 10 wherein the first cap is charged with the bactericide in a granular form.

12. The improvement of claim 10 wherein the first cap is charged with the bactericide in a caked form.

13. The improvement of claim 10 wherein the bactericide contains chlorine.

14. The improvement of claim 13 wherein the bactericide is sodium salt of dichloroisocyanuric acid.

15. The improvement of claim 10 wherein the resin is a large-pore, macroreticular, Type 1, quaternary ammonium, anion exchange resin.

16. The improvement of claim 15 wherein the bactericide is sodium salt of dichloroisocyanuric acid.

17. The improvement of claim 16 wherein the first cap is charged with not less than approximately one gram of sodium salt of dichloroisocyanuric acid as the bactericide by dry weight, for each ten grams of the resin, by dry weight.

18. The process of any of claims 11, 12, 13, 14, 15, 16 or 17 wherein the inlet is connected in step (b) to a source of water from which bacteria are to be removed.

19. An ion exchange cartridge for removal of bacteria from water comprising: a housing having a water inlet and a water outlet and defining a chamber therebetween; a highly water-soluble bactericidal preconditioning agent contained within said chamber at a first location; an ion exchange resin particularly adapted to remove bacteria from water and located in a second portion of said chamber, whereby when water is initially flowed into said inlet, through said chamber and out of said outlet said bactericidal agent is rapidly dissolved and sterilizes portions of said cartridge including said chamber and said outlet located downstream from said first location and whereby said bactericidal agent is rapidly exhausted so that upon complete depletion of said bactericidal agent said ion exchange material adsorbs bacteria from said water and said water remains substantially free of any bactericidal agent.

20. An ion exchange cartridge for the removal of bacteria from water as defined in claim 19 wherein said bactericidal agent is comprised of a salt of dichloroisocyanuric acid.

21. An ion exchange cartridge for removing bacteria from water as defined in claim 20 wherein said salt of said dichloroisocyanuric acid is a sodium salt of dichloroisocyanuric acid.

22. A method of treating a bacteria removing ion exchange cartridge to sterilize portions of said cartridge downstream of a bactericide comprising the steps of: loading a highly water-soluble bactericidal agent within a chamber of said cartridge, said chamber also containing a bacteria removing ion exchange resin; flowing a stream of contaminated water into said cartridge; contacting said bactericide with said water; dissolving said bactericide in said water rapidly and completely; sterilizing with said dissolved bactericide all portions of said chamber downstream of said bactericide; flushing said cartridge free of bactericide; and adsorbing bacteria from said water with said ion exchange resin to provide purified water without bactericide.

23. A method of treating a bacteria removing ion exchange cartridge to sterilize portions of said cartridge downstream of a bactericide as defined in claim 22 wherein the step of loading said cartridge with said highly water-soluble bactericidal agent comprises the step of loading said cartridge with a sodium salt of dichloroisocyanuric acid.

24. A method of removing bacteria from a stream of liquid using a replaceable cartridge of ion exchange resin comprising loading a replaceable cartridge with an ion exchange resin having the capacity of adsorbing bacteria and with a highly soluble bactericide, inserting said cartridge into a fluid conduit whereby the fluid in said conduit passes into contact with said resin and said bactericide, dissolving said bactericide in said water rapidly and completely; sterilizing with said dissolved bactericide all portions of said replaceable cartridge downstream of said bactericide; flushing said replaceable cartridge free of bactericide; and adsorbing bacteria from said fluid stream with said ion exchange resin to provide a purified fluid stream without bactericide.

* * * * *